US006063978A

United States Patent [19]

Hotier et al.

[11] Patent Number: 6,063,978

[45] **Date of Patent: *May 16, 2000**

[54] PROCESS FOR SEPARATING PARAXYLENE COMPRISING AT LEAST ONE CRYSTALLIZATION STAGE AT HIGH TEMPERATURE AND AT LEAST ONE CLAY TREATMENT UPSTREAM FROM THE ADSORPTION ZONE

[75] Inventors: Gérard Hotier, Rueil Malmaison; Paul Mikitenko, Noisy le Roy, both of France; Stuart R MacPherson, Piedmont, Calif.

[73] Assignee: Institut Francais du Petrole, France

[ * ] Notice: This patent is subject to a terminal disclaimer.

[21] Appl. No.: 08/860,559

[22] PCT Filed: Dec. 27, 1995

[86] PCT No.: PCT/FR95/01738

§ 371 Date: Jun. 30, 1997

§ 102(e) Date: Jun. 30, 1997

[87] PCT Pub. No.: WO96/20907

PCT Pub. Date: Jul. 11, 1996

[30] Foreign Application Priority Data

Dec. 29, 1994 [FR] France .................................. 94 15896

[51] Int. Cl.[7] .............................. C07C 7/14; C07C 7/12; C07C 5/22

[52] U.S. Cl. .......................... 585/814; 585/812; 585/815; 585/479; 585/820; 585/828

[58] Field of Search .................................... 585/812, 813, 585/814, 815, 479, 820, 828

[56] References Cited

U.S. PATENT DOCUMENTS

| | | | |
|---|---|---|---|
| 3,729,523 | 4/1973 | Grandio, Jr. et al. | 260/674 A |
| 5,284,992 | 2/1994 | Hotier et al. | 585/805 |
| 5,329,061 | 7/1994 | Swift | 422/222 |
| 5,401,476 | 3/1995 | Hotier et al. | 585/805 |

*Primary Examiner*—Walter D. Griffin
*Assistant Examiner*—Thuan D. Dang
*Attorney, Agent, or Firm*—Millen, White, Zelano & Branigan, P.C.

[57] ABSTRACT

A process for separating paraxylene at very high purity from a charge of xylene isomers, comprising a selective adsorption of a fraction that is rich in paraxylene, at least one high-temperature crystallization of this fraction, and an isomerization of the fraction depleted of paraxylene, recycling the mother liquor to the selective adsorption optionally via a clay treatment followed optionally by a distillation of the treatment effluent, and optionally introducing the mother liquor into a distillation unit, wherein the crystallization can comprise several high-temperature stages.

46 Claims, 6 Drawing Sheets

PROCESS FOR SEPARATING PARAXYLENE COMPRISING AT LEAST ONE CRYSTALLIZATION STAGE AT HIGH TEMPERATURE AND AT LEAST ONE CLAY TREATMENT UPSTREAM FROM THE ADSORPTION ZONE

BACKGROUND OF THE INVENTION

The invention relates to a process for separating and preparing paraxylene from a mixture of aromatic hydrocarbons comprising xylene isomers.

The xylene isomers are orthoxylene, metaxylene, paraxylene and ethylbenzene. The main application of the invention is in obtaining paraxylene to a degree of purity that is sufficient for the synthesis, for example, of terephthalic acid, used in the preparation of synthetic fibers and particularly polyester.

The applicant has described in patent FR 2,681,066 (U.S. Pat. No. 5,284,992), which is incorporated as a reference, a process for separating and recovering paraxylene contained in a charge of hydrocarbons comprising essentially aromatic hydrocarbons having 8 carbon atoms.

This process comprises the combination of an enrichment step, and a purification, the enrichment is a selective adsorption on an adsorbent in a simulated moving bed of a charge containing essentially the xylene isomers, which makes it possible to substantially enrich a first adsorption effluent with paraxylene. The purification which is a crystallization, in at least one crystallization unit operating at high temperature, of the paraxylene-enriched effluent so as to obtain paraxylene having a very high purity, the mother liquor being recycled to the adsorption step.

This high temperature crystallization corresponds to the second crystallization step of conventional crystallization processes (Chevron; Arco) which generally comprise a first crystallization at low temperature (−40 to −70° C.) and a second crystallization to purify, at high temperature (0 to −20° C., for example), crystals obtained that were previously remelted.

Furthermore, a second fraction depleted of paraxylene and therefore enriched with ortho- and meta-xylene as well as ethylbenzene, delivered by the selective adsorption unit, is sent into an isomerization unit to increase its concentration of paraxylene to a value close to equilibrium and approximately close to or greater than the composition of the initial charge of hydrocarbons, and the isomerate obtained can then be recycled to the adsorption.

In the adsorption, crystallization and isomerization sequence described, various types of impurities can appear in the various effluents and cause disturbances in the operation of the units, which are detrimental to the yield obtained and to the purity of the paraxylene recovered.

First of all, during isomerization of the paraxylene-depleted fraction, olefinic hydrocarbons can be produced in a variable amount depending on the values of the partial pressures of hydrogen introduced. The subsequent formation of polymers and their passage into the adsorption unit can cause serious problems of circulation through the adsorbent, even deactivate it.

In addition, paraffinic and naphthenic hydrocarbons having 8 and 9 carbon atoms, whose volatility is between that of toluene, a desorption solvent for example, and that of the xylenes, are intermediate products of the conversion of ethylbenzene into xylenes during the isomerization and their accumulation can prove to be harmful.

Furthermore, aromatic hydrocarbons having 9 carbon atoms, present in low proportion and poorly separated in distillation columns, can be detrimental to the process. Such hydrocarbons include aldehydes and ketones that are heavier than the initial charge, which are formed when oxygen is accidentally dissolved.

Finally, another problem is linked to the presence of methanol. This alcohol is sometimes added in low proportion in mixtures of xylenes to be crystallized to prevent the cocrystallization of water and paraxylene.

Actually, the dry $C_8$-aromatic mixtures are relatively hygroscopic and when the suspension of paraxylene crystals in the mother liquor passes into the centrifuges, water contained in the ambient air can be absorbed into the mother liquor and this water can possibly crystallize in conjunction with the temperature of this mother liquor.

SUMMARY OF THE INVENTION

In addition, some exchangers can have leaks and some water can accidentally pass into the mixture to be crystallized.

The object of the invention is to eliminate these drawbacks and in particular to limit how much of these various impurities the adsorption section contains to seek to optimize it, to the extent that the adsorbent is very sensitive to the impurities of the charge of the adsorption zone. Another object of the invention is to improve the recovery of the paraxylene produced and to minimize the energy cost, particularly of the purification step.

This invention relates to a process for separating and recovering paraxylene from a charge that can contain metaxylene, this process comprising, in combination, an adsorption operation and a crystallization operation. According to the invention, at least a portion of the charge and/or of the products resulting from the crystallization, for example the mother liquor, undergo a clay treatment operation. At least a portion of the effluent resulting from the clay treatment operation is recycled to undergo an adsorption operation.

This invention also applies to a process comprising, in combination, besides the operations of adsorption and crystallization, an isomerization step. In this case, at least a portion of the isomerate can be clay treated.

This invention relates, moreover, to a process for separating and recovering paraxylene from a charge that can contain metaxylene, this process comprising, in combination, an adsorption operation and a crystallization operation. According to this process, at least a portion of the mother liquor coming from the crystallization operation is purified by distillation before being recycled to the adsorption operation.

The invention relates also to a process for separating and recovering paraxylene contained in a charge of hydrocarbons comprising $C_8$-aromatic hydrocarbons, a process in which in particular:

in at least one adsorption zone, said charge containing at least metaxylene, paraxylene is put in contact with at least one adsorbent in the presence of at least one suitable desorption solvent under adsorption conditions such that there is obtained a first fraction containing solvent, metaxylene and optionally ethylbenzene and/or orthoxylene and a second fraction containing solventand the substantially enriched paraxylene;

the first fraction is distilled to recover a mixture of metaxylene and optionally ethylbenzene, and/or orthoxylene;

said mixture is isomerized at least in part under suitable conditions in at least one isomerization zone and an isomerate is recovered that is recycled at least partially to the adsorption zone;

said second fraction is distilled to obtain substantially enriched paraxylene and a crystallization of the substantially enriched paraxylene is performed obtaining, on the one hand, a mother liquor that is at least partially recycled to the adsorption step and, on the other hand, paraxylene crystals.

The process is characterized in that at least a portion selected from at least in part the charge, at least in part the isomerate and at least in part the mother liquor is made to circulate in at least one clay, or equivalent material, treatment zone and a first effluent is recovered that is introduced at least in part into the adsorption zone to produce said first and second fractions that are drawn off from the adsorption zone.

More specifically, the invention relates to a process for separating and recovering paraxylene contained in a charge of hydrocarbons comprising $C_8$-aromatic hydrocarbons, the process comprising the following steps:

a) in an adsorption zone, said charge containing metaxylene, paraxylene and optionally ethylbenzene and/or orthoxylene is. put in contact with an adsorbent in the presence of a suitable desorption solvent under adsorption conditions such that a first fraction containing solvent, metaxylene and optionally ethylbenzene and/or orthoxylene and a second fraction containing solvent and substantially enriched paraxylene are obtained;

b) the first fraction is distilled to separate the solvent on the one hand, and the mixture of metaxylene and optionally ethylbenzene, and/or orthoxylene, on the other hand;

c) said mixture is isomerized under suitable conditions in an isomerization zone and an isomerate is recovered that is recycled at least in part to step a);

d) the second fraction is distilled and the solvent on the one hand, and substantially enriched paraxylene, are recovered;

e) a crystallization of the paraxylene of step d) is performed in at least one crystallization zone at high temperature, advantageously between +10° C. and −25° C. and there is obtained, by separation, on the one hand, a mother liquor that is recycled at least in part to step a) and, on the other hand, paraxylene crystals saturated with mother liquor;

f) the paraxylene crystals are washed with a suitable washing solvent in at least one washing zone and paraxylene crystals having a very high degree of purity are recovered the process being characterized in that at least a portion selected from the charge, the isomerate and the mother liquor is made to circulate in at least one clay treatment zone and a first effluent is recovered that is introduced into the adsorption zone to produce said first and second fractions of step (a).

By high-temperature crystallization of paraxylene is meant a crystallization of a solution or suspension of paraxylene that is already paraxylene-enriched, which corresponds to what the literature calls a purification step. For example, the U.S. Pat. No. 2,866,833 that is incorporated as a reference, mentions a step for purifying paraxylene that can go up to −34° C.

At least a portion of the charge of hydrocarbons can be pretreated in a clay-treatment reactor. It can be advantageous to put the isomerate in a clay-treatment reactor before being sent into the adsorption. These reactors can be independent or form only a single reactor, optionally common with the one that treats the mother liquor.

These clay treatments make it possible to eliminate at least in part the olefins created in particular in the isomerization step and at least a portion of the heavy impurities, which circulate in the adsorption, crystallization and isomerization loop.

Various variants can be envisioned:

The mother liquor can be advantageously introduced at least in part into a distillation column downstream from the isomerization zone. This column also treats the effluent of the isomerization zone and delivers a top fraction containing light compounds ( water, methanol, $C_7$—) and another fraction containing a distilled mixture of mother liquor and isomerate that is then introduced into the clay treatment zone.

A distillation bottom fraction containing heavy compounds can also be drawn off from this distillation column, which makes it possible to reduce the size of the downstream equipment.

A portion of the mother liquor can also be mixed with the effluent, whatever it is, leaving the clay treatment zone, whether this is the effluent resulting from the circulation of the isomerate, the mother liquor and the charge in the clay treatment zone, or the effluent resulting from the circulation, in the clay treatment zone, of the latter and of the distillation fraction containing said distilled mixture of mother liquor and isomerate, before being introduced into the selective adsorption zone.

The resulting effluent of the latter variants can be distilled in at least one distilling column (a so-called rerun column) that delivers a bottom fraction containing heavy compounds and a top fraction that is introduced into the adsorption zone optionally with a portion of the mother liquor.

The conditions for adsorbing or eliminating the undesirable compounds on the clay are, as a general rule, the following:

Temperature: 100 to 300° C., preferably 160 to 230° C.

Hourly space velocity: 1 to 8, preferably 1 to 4 (Hourly volume of charge per volume of clay)

Type of clay natural aluminosilicates activated by acids, for example the clay referenced F54 with ENGELHARD.

Pressure: 3 to 100 bar, preferably 4 to 20 bar.

The distillation column, depending on the isomerization, generally has the following characteristics:

Pressure: 1 to 20 bar, preferably 3 to 8 bar

Base temperature: 150 to 280° C., preferably 200 to 240° C.

Number of plates: 30 to 80, preferably 50 to 70.

The distilling column, known as rerun, located between the clay treatment zone and the selective adsorption zone usually has the following characteristics:

Pressure: 1 to 20 bar, preferably 3 to 8 bar

Base temperature: 160 to 290° C., preferably 210 to 250° C.

Number of plates: 40 to 200, most often 50 to 90.

According to another characteristic of the invention, it is possible to keep the amount of constituents with intermediate volatility at a tolerable level. In this case, at least a portion of the mother liquor can be purged before being introduced into the clay treatment zone.

It can also be advantageous to purge at least in part the desorption solvent resulting from distillation steps (b) and (d) of the depleted fraction or of the paraxylene-enriched fraction before it is recycled and to compensate for the purge of the solvent by an addition of fresh solvent, either into the charge or upstream from the adsorption zone.

As has been indicated, it is possible to recycle the crystallization mother liquor in different places of the installation depending on the magnitude of the amount of undesirable compounds, but it can be advantageous to combine these different recyclings with one another, for example, when it involves reusing existing pieces of equipment for the distillation of the isomerate, the clay treatment or the so-called rerun distillation and when one of these pieces of equipment is already operated at its maximum flow rate.

It is also possible to combine these different recyclings and these purges when it is desired to have the amount of an impurity in the loop reduced without seeking to eliminate it altogether.

The crystallization step of the paraxylene-enriched fraction is generally performed, as has been mentioned above, at high temperature, for example between +10 and −30° C. and preferably +10 and −25° C. The temperature is usually selected as a function of the concentration of paraxylene that it is desired to have in the mother liquor, and of the economic cost of the crystallization operation.

It is possible under these conditions to perform a crystallization of the paraxylene in a single stage when the paraxylene that is collected, for example as an extract of the adsorption unit, has a purity greater, for example, than 85%.

But it can be advantageous, particularly for economic reasons, to perform a crystallization in several stages, for example a first crystallization at a temperature T1 between +10 and −10° C., and a second crystallization at a temperature T2, lower than T1, between 0 and −25° C.

According to a first embodiment of the invention, a crystallization of the paraxylene of step (d) is performed in a single stage, a suspension of crystals in the mother liquor is recovered, the crystals are separated from the mother liquor in a separation zone, the crystals obtained are washed with the washing solvent, a washing liquor is recovered, at least a portion of the mother liquor and at least a portion of the washing liquor are recycled and the paraxylene crystals are melted completely so as to obtain a liquid stream of melted paraxylene.

According to a second embodiment that uses a first variant of a two-stage crystallization of the paraxylene-enriched fraction, a first crystallization of the paraxylene of step (d) is performed in a first crystallization zone at a temperature T1, a suspension of first paraxylene crystals in a first mother liquor is recovered, the first crystals are separated from the first mother liquor in a first separation zone, at least a portion of the first mother liquor is recycled to the adsorption zone, the separated first crystals are melted and they are crystallized in a second crystallization zone at a temperature T2 that is higher than T1, a suspension of second paraxylene crystals in a second mother liquor is recovered, the second crystals are separated from the second mother liquor in a second separation zone, the second crystals are washed with the suitable washing solvent in the second separation zone, a washing liquor is recovered, the second mother liquor, at least in part, and at least a portion of the washing liquor are recycled to the first crystallization zone and optionally in part to the second crystallization zone and the second paraxylene crystals are melted completely so as to obtain a liquid stream of melted paraxylene.

For example, temperature T1 of the first crystallization can be −5 to −25° C. while temperature T2 of the second crystallization can be +10 to −5° C.

According to another embodiment of the invention, using a second variant of a two-stage crystallization, a first crystallization of the paraxylene of step (d) is performed in a first crystallization zone at a temperature T1, a suspension of first paraxylene crystals in a first mother liquor is recovered, the first crystals are separated from the first mother liquor in a first separation zone, optionally the first crystals are washed with the washing solvent in the first separation zone, at least a portion of the first mother liquor is crystallized in a second crystallization zone at a temperature T2 that is lower than temperature T1, a suspension of second paraxylene crystals in a second mother liquor is recovered, the second crystals are separated from the second mother liquor in a second separation zone, the second crystals are washed with the washing solvent in the second separation zone, a second mother liquor is recovered that is recycled at least in part to the adsorption zone, the first and second paraxylene crystals are mixed, they are melted completely and a stream of melted paraxylene is recovered.

For example, the first crystallization can be performed at a temperature T1 between +10 and −10° C. while the second T2, which is lower than T1, can be performed between 0 and −25° C.

According to another embodiment of the invention comprising a crystallization having several stages, a first crystallization of the paraxylene of stage (d) and of recycled partially melted or possibly melted crystals coming from a second crystallization afterward is performed in a first crystallization zone at a temperature T1, a suspension of paraxylene crystals in a first mother liquor is recovered, the crystals are separated from the first mother liquor in a first separation zone, said crystals are washed, they are melted and a stream of melted paraxylene is recovered, at least a portion of the first mother liquor is crystallized in a second crystallization zone at a temperature T2 that is lower than temperature T1, a suspension of second paraxylene crystals in a second mother liquor is recovered, the second crystals are separated from the second mother liquor in a second separation zone, a second mother liquor is recovered that is recycled at least in part to the adsorption zone, optionally the second crystals are melted and the optionally melted crystals are recycled to the first crystallization zone to recrystallize them with the paraxylene of step (d) at temperature T1.

Another variant may consist to partially melt the second crystals and to recycle the so-obtained slurry to the first crystallization zone to recrystallize it with the paraxylene of step (d) at temperature T1.

According to another particularly advantageous embodiment of the invention, a first crystallization of the paraxylene of step (d) is performed in a first crystallization zone at a temperature T1, a suspension of first paraxylene crystals in a first mother liquor is recovered, the first crystals are separated from the first mother liquor in a first separation zone, at least a portion of the first mother liquor is crystallized in a second crystallization zone at a temperature T2 that is lower than T1, the second crystals are separated from the second mother liquor in a second separation zone, the second mother liquor is recovered that is recycled at least in part to the adsorption zone, the first crystals and the second crystals are recovered and they are washed in at least one separation and countercurrent washing zone with the suitable washing solvent, a washing liquor which is recycled at least in part to the first crystallization zone is recovered on the one hand, paraxylene crystals are recovered on the other hand, they are melted completely in a melting zone and a stream of melted paraxylene is collected.

The invention also relates to a process for separating and recovering paraxylene contained in a charge of hydrocarbons comprising $C_8$-aromatic hydrocarbons, the process comprising the following steps:

a) in at least one adsorption zone (8), said charge (1) containing metaxylene, paraxylene and optionally ethylbenzene and/or orthoxylene is put in contact with an adsorbent in the presence of a suitable desorption solvent under adsorption conditions such that there is obtained a first fraction containing solvent, metaxylene and optionally ethylbenzene and/or orthoxylene and a second fraction containing solvent and essentially substantially enriched paraxylene;

b) the first fraction is distilled (12) to separate the solvent on the one hand, and the mixture of metaxylene and optionally ethylbenzene, and/or orthoxylene, on the other hand;

c) said mixture is isomerized under suitable conditions in an isomerization zone (21) and an isomerate (2) is recovered that is recycled at least in part to step a);

d) the second fraction is distilled (16) and the solvent on the one hand, and substantially enriched paraxylene, are recovered;

e) a crystallization of the paraxylene of step d) is performed in at least one crystallization zone (5*a*, 5*b*) at high temperature, advantageously between +10° C. and −25° C. and there is obtained, by separation, on the one hand, a mother liquor that is recycled (3) at least in part to step a) and, on the other hand, paraxylene crystals saturated with mother liquor;

f) the paraxylene crystals are washed with a suitable washing solvent in at least one washing zone and paraxylene crystals having a very high degree of purity are recovered the process being characterized in that at least a portion of the mother liquor (3) (33) is introduced into a distillation column, a fraction containing purified mother liquor is obtained, a fraction which is then sent into the adsorption zone (8).

Of course, one will not go outside the scope of this invention by using a desorption solvent other than toluene such as in particular paradiethylbenzene (PDEB), this solvent, being heavier than the xylenes, will be recovered at the bottom of certain columns while the toluene was recovered at the top.

The invention will be better understood in view of the following figures that illustrate in a nonlimiting way several embodiments of the invention, of which:

FIG. 1 diagrammatically represents the process and the various possibilities for recycling the isomerate and the crystallization mother liquor to the adsorption via a clay treatment.

DETAILED DESCRIPTION OF THE DRAWINGS

Figure 1:
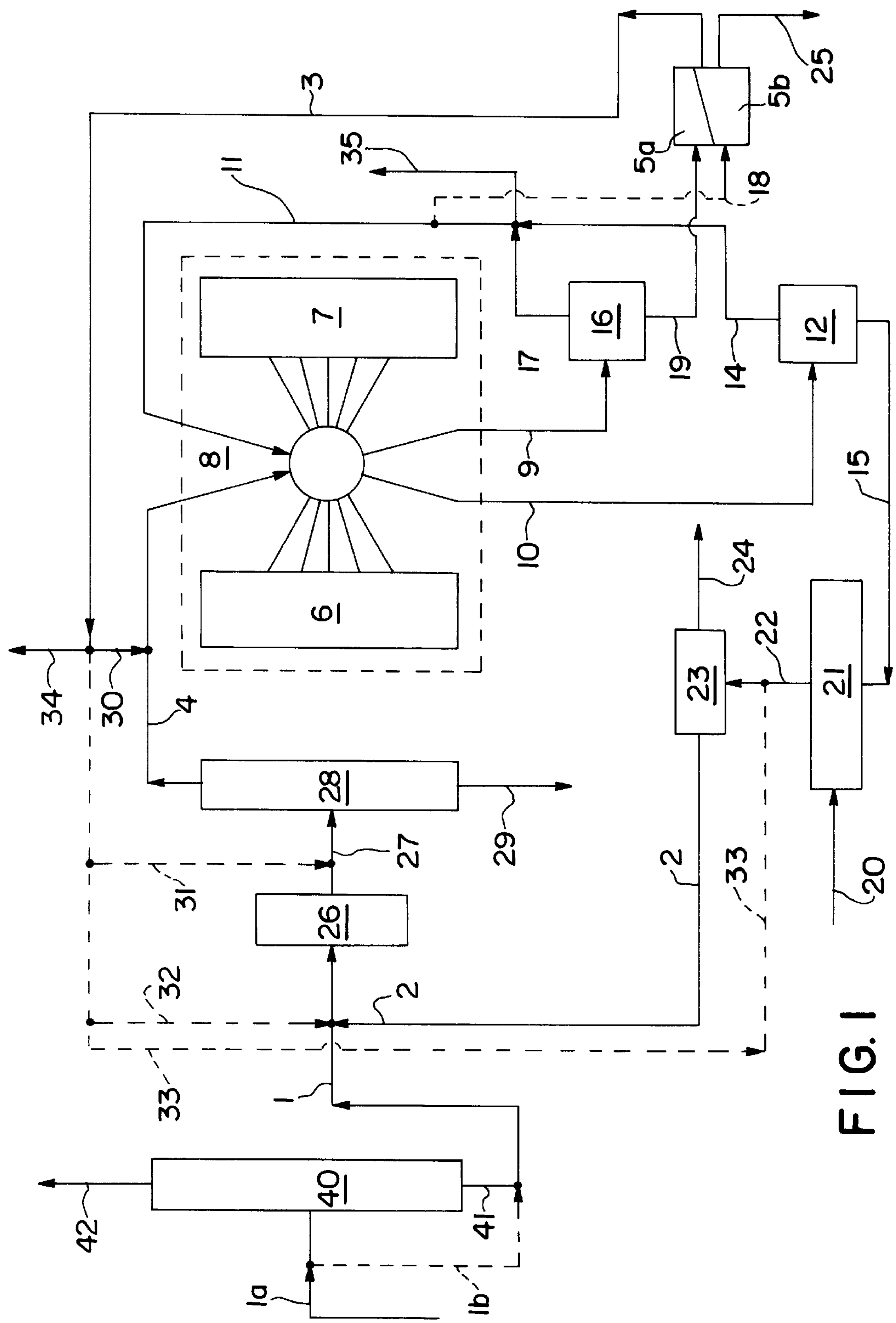

The operating conditions and the adsorption in simulated moving bed (countercurrent, for example) are selected so that the first fraction containing metaxylene, orthoxylene and ethylbenzene is a raffinate and the second fraction containing essentially paraxylene is an extract. These conditions are described in the U.S. Pat. No. 5,284,992.

By a line 1, a charge is conveyed that comprises about 20% ethylbenzene, 18% paraxylene, 45% metaxylene and 17% orthoxylene. Joined to it by a line 2 is a recycled effluent whose ethylbenzene content is appreciably lower, typically 8 to 13%, and which contains impurities. By lines 3 and 30, another recycled effluent is introduced whose paraxylene content is greater, typically 25 to 45%. A line 4 recovers the charge and these two effluents, it conveys a mixture of approximate composition, paraxylene 20 to 22.5, ethylbenzene 9 to 14%, orthoxylene 20 to 22.5%, metaxylene 45 to 50%, which is introduced into a simulated countercurrent adsorption zone 8 comprising one or more columns 6 and/or 7 filled with a zeolitic adsorbent, each of the columns being divided into a limited number of beds, the number of the beds of each column being able to be between 4 and 20, the productivity, expressed in relation to the paraxylene produced, being about 0.07 $m^3$ per $m^3$ of sieve and per hour expressed at ambient conditions. Desorbing is by toluene, at a rate of about 1.45 $m^3$ of toluene per $m^3$ of charge, the operating temperature being approximately 160° C. Drawn off from this unit by a line 10 is a paraxylene-depleted raffinate containing essentially toluene, metaxylene, ethylbenzene and orthoxylene and, by a line 9, an extract of paraxylene-enriched composition containing essentially toluene and paraxylene, the major impurity being ethylbenzene. The raffinate is introduced into a distilling column 12 (top temperature 125° C., bottom temperature 160° C., for example). Drawn off at the top by a line 14 is toluene (about 30% of the amount introduced, into the adsorption, for example) containing for example less than 2% of $C_8$-aromatic compounds and, drawn off at the bottom of this column by a line 15, is a liquid (raffinate free of solvent) rich in ethylbenzene, metaxylene and orthoxylene and depleted of paraxylene (less than 3%, for example) that is sent into an isomerization unit 21. This raffinate is put in contact with hydrogen introduced by a line 20 and with a catalyst having a base of mordenite and platinum on aluminum at about 380° C. A line 22 conducts the isomerate from the outlet of the reactor to a flask for separating the gaseous constituents (not shown in the figure), then to a distilling column 23 (top temperature 90° C., bottom temperature 160° C., for example). Drawn off at the top by a line 24 are $C_1$ to $C_5$ hydrocarbons, hexane, cyclohexane, benzene and toluene and at the bottom of this column by a line 2, an effluent containing 8 to 13% ethylbenzene, 21 to 24% paraxylene, 21 to 24% orthoxylene, 45 to 50% metaxylene and impurities, which is recycled to adsorption zone 8.

Line 9 introduces the extract into a distilling column 16 from which toluene having less than 2% $C_8$-aromatic compounds (about 70% of the amount introduced, into the adsorption, for example) is drawn off at the top and is recycled by lines 17 and 11 to the feed of desorption solvent of the adsorption unit. At the bottom of column 16 at about 160° C., a stream enriched with paraxylene (at about 90% paraxylene) is drawn off by means of a line 19 which conducts it into a one-stage crystallization unit 5*a*, 5*b* for example operating at about −10° C. In this unit 5*a*, 5*b*, paraxylene crystals are produced which are in suspension in a mother liquor. The crystals are separated in at least one centrifuge 5*b* for example and washed in the centrifuge. On the one hand, a paraxylene-depleted (about 54%) mother liquor is collected which is recycled by line 3 to adsorption zone 8 via clay-treatment and distillation zones discussed below and, on the other hand, paraxylene crystals, that are melted, are collected. The washing solvent, toluene for example, is brought by a line 18 and can, as shown in the figure, come from the distillation unit of raffinate 12 and/or from the unit for distillation of extract 16. There is recovered from unit 5*b*, after a distillation of the melted crystals not shown, liquid paraxylene with a purity for example equal to 99.75% by a line 25 and toluene that is recycled (line not shown).

Figure 2:
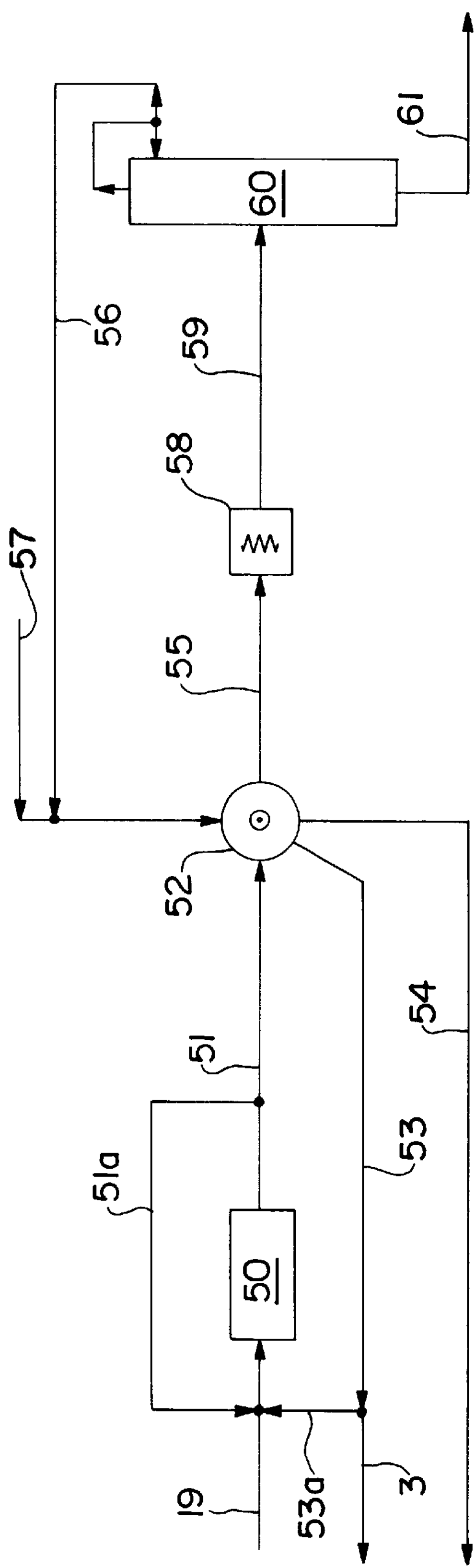
FIGS. 2 and 3 illustrate a purification of paraxylene by crystallization in a single stage.

FIG. 2 illustrates more precisely the steps of crystallization and of downstream treatment of the paraxylene crystals with a washing with toluene. According to this figure, crystallization unit 50 in a single stage receives the crystallization charge (the distilled extract) by line 19. Crystals in suspension in a mother liquor are recovered by a line 51 and are separated at least in part in at least one centrifuge 52. A mother liquor containing for example 54% paraxylene is drawn off and recycled at least in part to adsorption zone 8 by lines 53 and 3, another part being able to be recycled to crystallization zone 50 by a line 53*a*. A portion of the crystals in suspension in the mother liquor can also be recycled in the crystallization zone by a line 51*a*.

Then, recycled toluene coming from a distillation column 60 brought by a line 56, and toluene brought by a line 57 of fresh solvent coming from line 18 are introduced into centrifuge 52 as washing solvent. A washing liquor is collected separately by a line 54 that is connected to centrifuge 52, and it is recycled at least in part in the unit for distilling raffinate 12.

The washed crystals of paraxylene are drawn off by a line 55, completely melted in a melting zone 58 and introduced into distillation column 60 by a line 59. At the bottom of the column, liquid paraxylene of very high purity is recovered, and at the top of the column, toluene is recovered which is recycled at least in part into centrifuge 52. At least one centrifuge was used to separate the crystals and the mother liquor. Also, at least one rotary filter could have been used instead of the centrifuge.

According to a variant that is not shown, the centrifuge can be replaced by at least one column for separating and countercurrent washing, cited in the U.S. Pat. Nos. 4,475,355, and 4,481,169, the NIRO column for example, incorporated by reference. In this case, the mother liquor and the washing liquor are one and the same liquor which is optionally distIlled before being recycled, at least in part, to the adsorption zone, via the clay treatment and distillation zones, and optionally in part in the crystallization zone.

Figure 3:
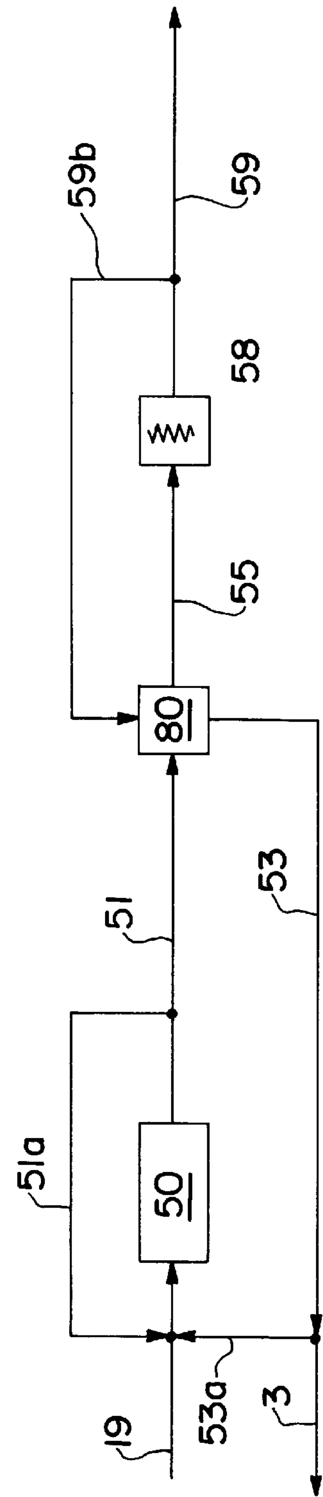

According to another variant illustrated by FIG. 3, it is possible to use another washing solvent such as the melted paraxylene coming from melting zone 58. In this case of a figure having the same references for the same elements as those of FIG. 1, at least a portion of the melted paraxylene is introduced countercurrent of suspension 51, by a line 59*b*, into a countercurrent column 80, a NIRO-type column for example, and is used to wash the paraxylene crystals in the column. At least a portion of the melted paraxylene that is introduced into the column crystallizes there.

The crystals recovered from the column by line 55 are then melted in melting zone 58 and the liquid paraxylene of very high purity is recovered by line 59.

The washing liquor and the mother liquor are recovered at the same time by line 53 and are recycled to adsorption zone 8, a portion being able to be recycled to crystallization zone 50.

If a washing solvent, for example pentane, other than the desorption solvent (toluene) and melted paraxylene, were used, the process described according to FIG. 2 would be reproduced, except that the washing liquor coming from centrifuge 52 would have to be freed of solvent by a subsequent distillation (not shown in the figure) before being recycled to the adsorption or to the crystallization. The distilled solvent is then recycled into the centrifuge.

The process according to FIG. 3 could also be reproduced with a countercurrent washing column and a washing solvent other than the melted paraxylene and the desorption solvent. In this case, after complete melting of the crystals, a stream of melted paraxylene containing washing solvent is distilled, solvent is recovered, at the top, that is recycled at least in part in the washing column and, at the bottom, paraxylene of very high purity is recovered. The mother liquor comprising the washing liquor is drawn off from the washing column, distilled and recycled at least in part to the selective adsorption zone and optionally in part to the crystallization zone.

Figure 4:
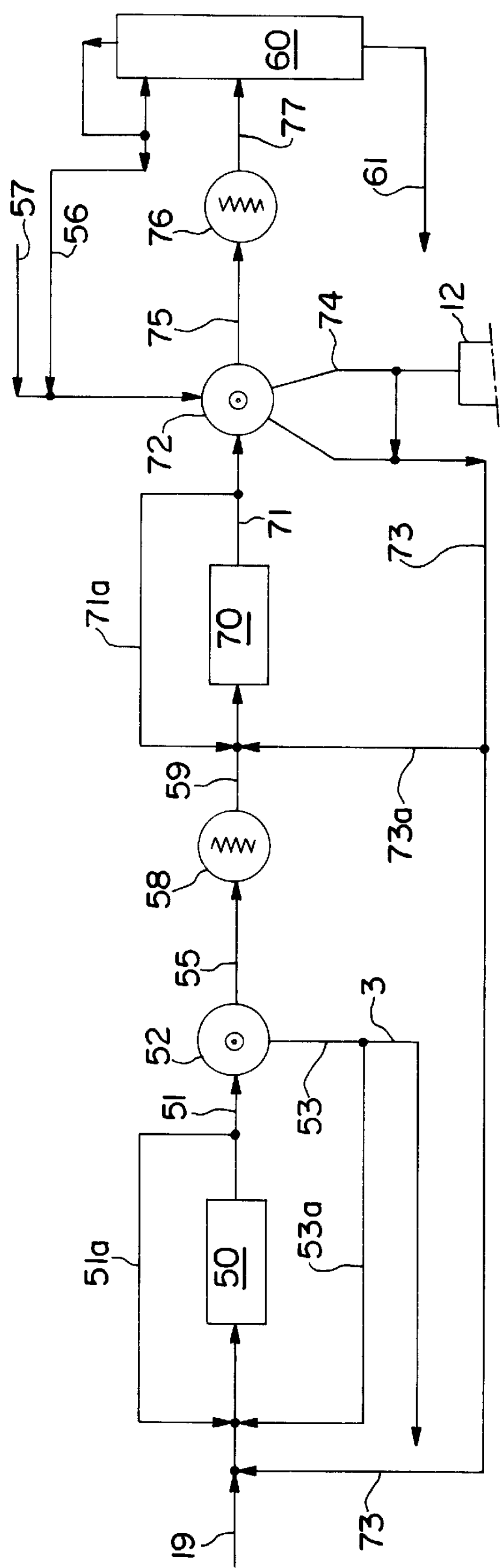
FIGS. 4 and 5 show a purification of paraxylene by crystallization in a double stage, the first being colder than the second.
Figure 5:
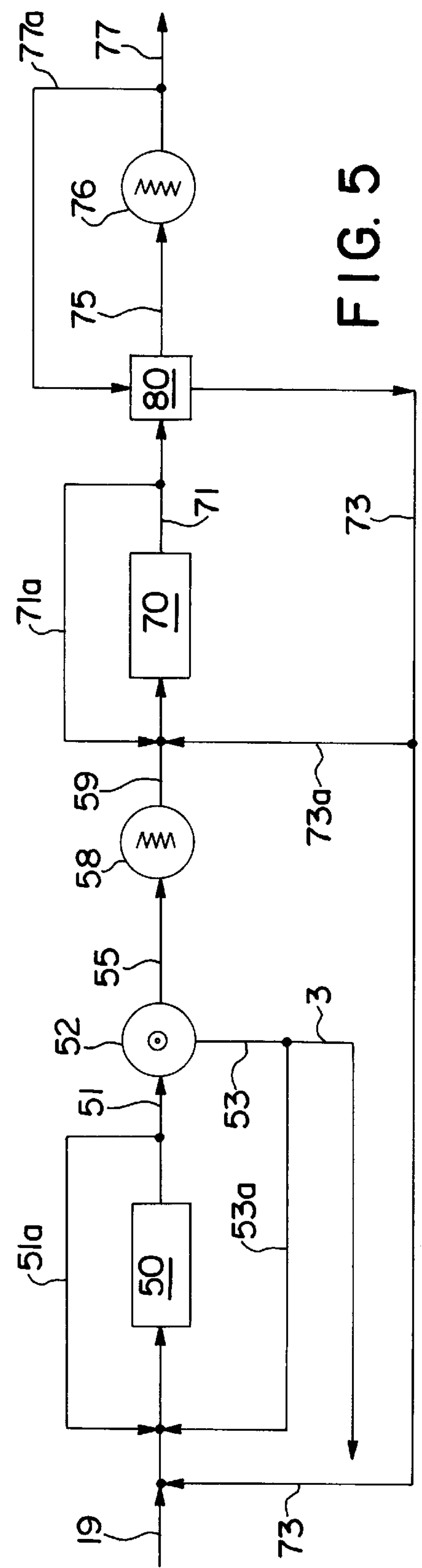

FIGS. 4 and 5 illustrate a two-stage crystallization, the temperature of the second crystallization stage being higher than that of the first stage. According to FIG. 4, the first crystallization unit 50, at –20° C. for example, receives the crystallization charge (the extract distilled from the adsorption) by line 19. Its purity is about 80%. Crystals in suspension in a mother liquor are recovered by a line 51 and are separated in a first centrifuge 52. A first mother liquor containing, for example, 40% paraxylene is drawn off and recycled at least in part to adsorption zone 8 by lines 53 and 3 via the clay treatment and distillation zones, the other part being able to be recycled to the first crystallization.

The crystals recovered by a line 55 are melted in a melting zone 58 and are introduced by a line 59 into a second crystallization unit 70 operating for example at 0° C. A suspension of second crystals is recovered by a line 71, and is introduced into at least a second centrifuge 72 or a rotary filter.

A second mother liquor is recovered, by a line 73, and is recycled at least in part to the first crystallization unit 50 and optionally in part to the second crystallization zone. The separated crystals are washed with the desorption solvent (toluene, for example) used as a washing solvent is introduced into the centrifuge by a line 56, and an added portion 57 coming from line 17 in particular, and a washing liquor 74 is drawn off that is recycled at least in part to the first crystallization unit 50 and/or to the second crystallization unit 70 after optionally having been distilled. It could also be recycled to the unit for distilling the raffinate (step b).

Furthermore, from a line 75 that is connected to centrifuge 72, the second crystals that are melted completely in a melting zone 76 are recovered, and melted paraxylene that is distilled in distilling column 60 is collected by line 77. The toluene recovered at the top is recycled by line 56 while the paraxylene of very high purity is drawn off at the bottom of the column by line 61.

Centrifuge 72 could be replaced with a countercurrent washing column. In this case, the second mother liquor containing washing toluene can be distilled, as is the case with a single stage before being recycled, and the washing toluene sent back to the washing column.

FIG. 5 illustrates the use of a countercurrent column, of the NIRO column type, as a second zone for separation and washing of the second crystals, instead of centrifuge 72 of FIG. 4 or instead of a rotary filter, and which uses as washing solvent not toluene, but a portion of the melted paraxylene stream. According to this FIG. 5, comprising the same elements as those of FIG. 4, the second crystals in suspension in the second mother liquor are recovered by a line 71 coming from the second crystallization unit, and it is introduced into NIRO column 80 which is fed with washing solvent by a portion of the melted paraxylene that is collected by a line 77*a*. Paraxylene crystals of very high purity that are melted in melting zone 76 are collected by a line 75 and a stream of melted paraxylene is recovered by line 77. The second mother liquor having 70%, for example, paraxylene and the washing liquor are recovered at the same time and are recycled at least in part to the first crystallization unit 50 by a line 73 and optionally in part to the second crystallization unit.

According to another variant that is not illustrated by the figures, the washing solvent can be a solvent other than the stream of melted paraxylene and the desorption solvent, for example pentane. In this case, the stream of melted paraxylene is distilled so as to recover, at the top, washing solvent that is recycled at least in part in the second separation zone and, at the bottom, paraxylene of very high purity, the mother liquor comprising the washing liquor is distilled before being recycled to the first crystallization zone and optionally in part to the second crystallization zone if the second separation zone is a countercurrent washing column (a NIRO column, for example).

However, if the second separation zone is a centrifuge or a rotary filter, the mother liquor is recycled to the first crystallization zone and optionally in part to the second crystallization zone, and the washing liquor is distilled before being recycled to the first crystallization zone and optionally in part to the second crystallization zone.

A recycling of the first crystals in suspension 51*a* and of the second crystals in suspension 71*a* can be envisioned, respectively in the first and in the second crystallization zone.

Figure 7:
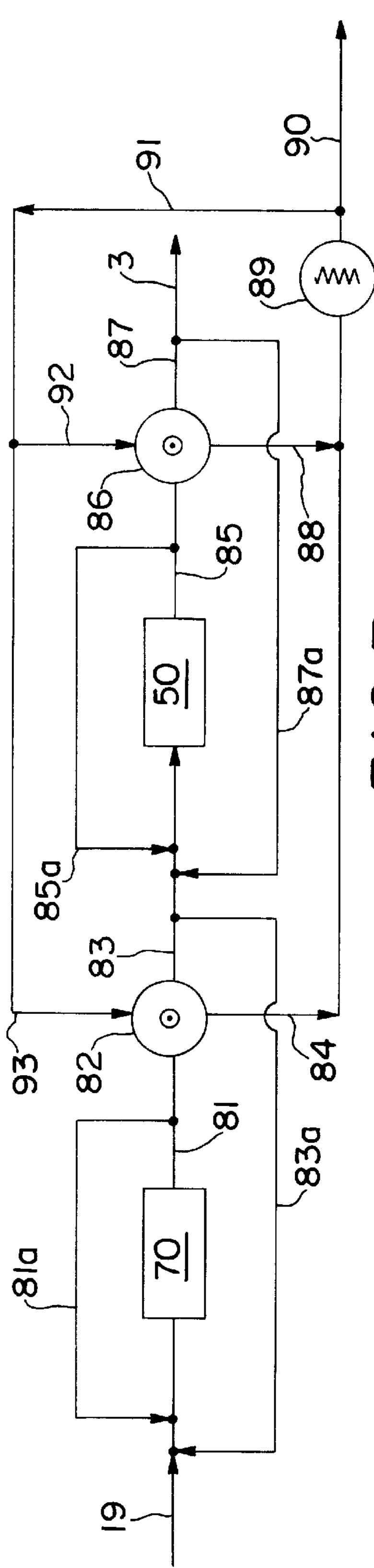
FIGS. 6 to 10 represent a purification of paraxylene by crystallization in a double stage, the first being hotter than the second.
Figure 6:
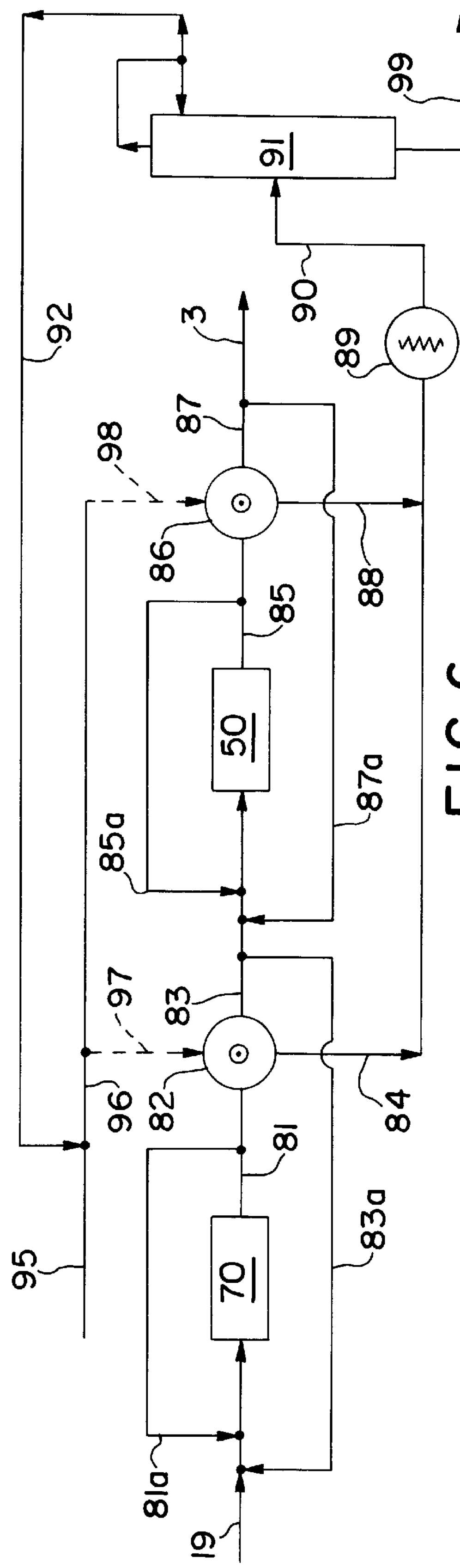

FIGS. 6 and 7 illustrate a two-stage crystallization of the paraxylene, the temperature of the second stage of crystallization of the mother liquor being lower than that of the first stage.

According to FIG. 6, the crystallization charge (the extract distilled from the adsorption) is introduced by line 19 into the first crystallization unit 70 which operates at about 0C. First crystals in suspension in a first mother liquor are recovered by a line 81, and are separated in at least one first centrifuge 82, washed by toluene brought by a line 97 and recovered by a line 84. The first mother liquor containing, for example, 70% paraxylene is introduced at least in part by a line 83 into the second crystallization unit 50 operating at −10° C. Another part can be recycled in the first crystallization unit by a line 83*a*. Second crystals in suspension in a second mother liquor are recovered by a line 85, and they are separated in at least one second centrifuge 86. They are collected by a line 88 after having been washed with toluene that has been introduced by a line 98 into the second centrifuge. The second mother liquor collected by line 87 contains a fraction of the washing toluene; it is recycled at least in part to adsorption zone 8 via the clay treatment and distillation zones and optionally in part by a line 87*a* to the second crystallization unit.

The first and second paraxylene crystals are mixed and introduced into a melting zone 89. A line 90 collects the melted paraxylene stream that is introduced into a distilling column 91 which delivers, at the bottom, paraxylene of very high purity and, at the top, toluene that is recycled by a line 92 and that is mixed with an added portion of toluene brought by a line 95 or line 18. The mixture of toluene obtained is introduced, at least in part, into each of centrifuges 82 and 86, as washing solvent.

FIG. 7 uses the same elements and the same references as FIG. 6, except that for the step of washing the crystals, very pure melted paraxylene recovered from line 90 is used as washing solvent. Actually, at least a portion of the very pure melted paraxylene is drawn off by a line 91 and introduced into first centrifuge 82 and into second centrifuge 86 to wash the first and second crystals, respectively. The first mother liquor and a first washing liquor are sent by line 83 into the second crystallization unit 50 while the second mother liquor and the second washing liquor are collected by line 87 to be recycled, at least in part, to adsorption zone 8.

In this figure, the use of centrifuges 82 and 86 to separate the crystals of the mother liquors and to wash them has been described, but they could also be replaced with countercurrent columns, of the NIRO column type. In this case, the respective solutions collected would gather together the mother liquor and the washing liquor coming from each column.

Figure 8:
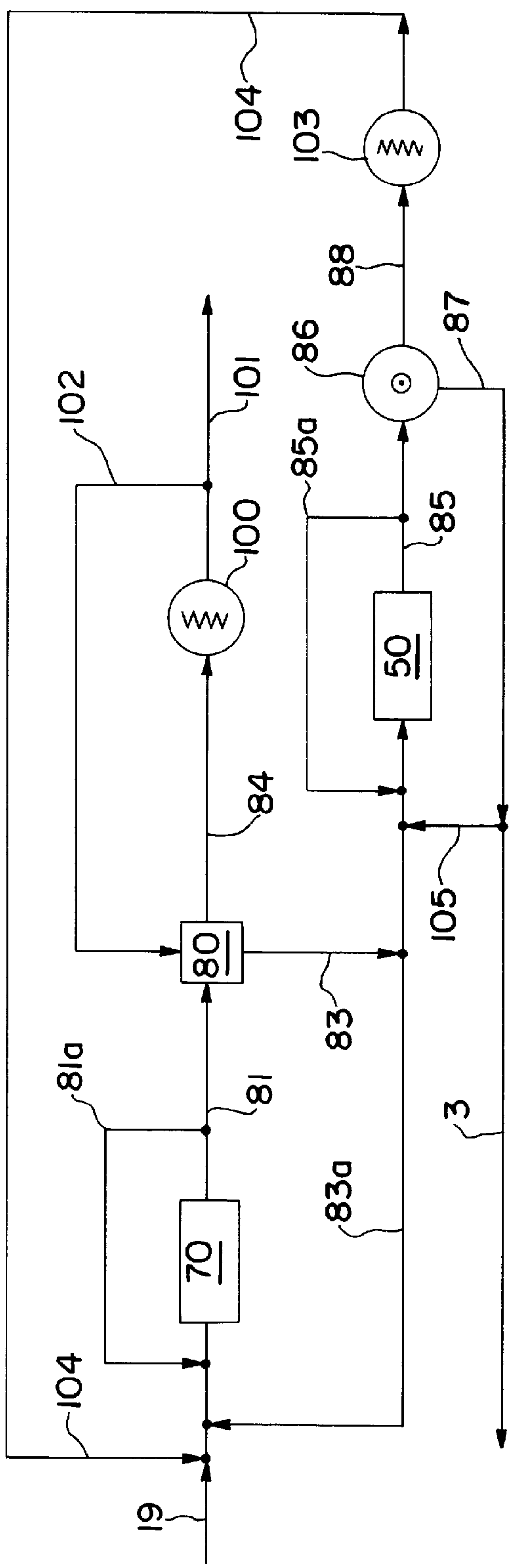

FIG. 8 illustrates another variant of the process having several crystallization stages, in which the melted paraxylene of very high purity is collected at the output of the crystallization zone at high temperature.

The crystallization charge (the extract distilled from the adsorption) is introduced by line 19 into the first crystallization unit 70 which operates at about 0° C. Crystals in suspension in a first mother liquor are recovered by a line 81, and are separated for example on a NIRO column 80, the crystals recovered by a line 84 being melted in a melting zone 100. A stream of melted paraxylene of very high purity is collected by a line 101, that is drawn off in part thanks to line 102 to wash the crystals in the NIRO column. The first mother liquor which is drawn off from the NIRO column by line 83 is introduced, at least in part, into a second crystallization unit 50 operating at a temperature of −15° C., for example. Another part of this first mother liquor can be recycled by a line 83*a* and mixed with the charge of the first crystallization unit.

From the second crystallization unit 50, a suspension of second crystals in a second mother liquor is collected by a line 85, that is separated in at least one centrifuge 86 or a rotary filter. A second mother liquor is recovered, by a line 87, that is recycled at least in part to adsorption unit 8 via the clay-treatment and distillation zones, a part being able to be recycled also to the second crystallization unit 50 by a line 105 connected to line 87.

The second crystals, once separated, are collected by a line 88 and melted optionally in a melting zone 103. The possibly melted paraxylene is recycled by a line 104 and mixed with the charge of the first crystallization unit 70 to be recrystallized at the temperature of the first crystallization.

Figure 9:
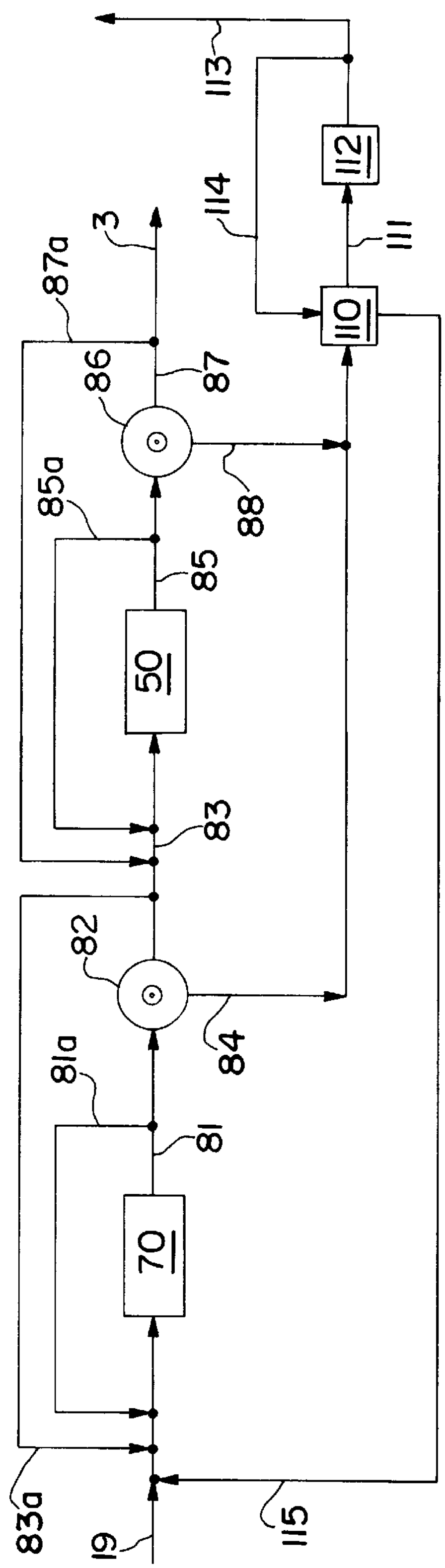

FIG. 9 represents a preferred variant of the two-stage crystallization process operating advantageously between +5 and −7° C. for the first and between −7 and −25° C. for the second.

The crystallization charge (the extract distilled from the adsorption) is introduced by line 19 into a first crystallization unit 70. First crystals in suspension in a first mother liquor are recovered by a line 81 and are separated in at least one centrifuge 82 or at least one rotary filter. The first mother liquor collected by line 83 is introduced at least in part into a second crystallization unit 50, another part being able to be recycled to the first crystallization unit 70. A second suspension of crystals is collected by a line 85, that is separated in at least one centrifuge or rotary filter 86. A second mother liquor is drawn off by a line 87 and recycled at least in part to adsorption zone 8 via the clay-treatment and distillation zones, another part being able to be drawn off and recycled to the second crystallization unit by a line 87*a* connected to line 87. The first and second crystals respectively collected by lines 84 and 88 are gathered together and introduced into at least one. washing column 110, of the NIRO column type, where they are washed by a washing solvent. Paraxylene crystals are collected by a line 111 which are completely melted in a melting zone 112 and a stream of paraxylene of very high purity is drawn off. A portion of the paraxylene stream is drawn off by a line 114 and introduced as washing solvent into column 110. The washing liquor collected in the column is recycled at least in part to the first crystallization unit.

Figure 10:
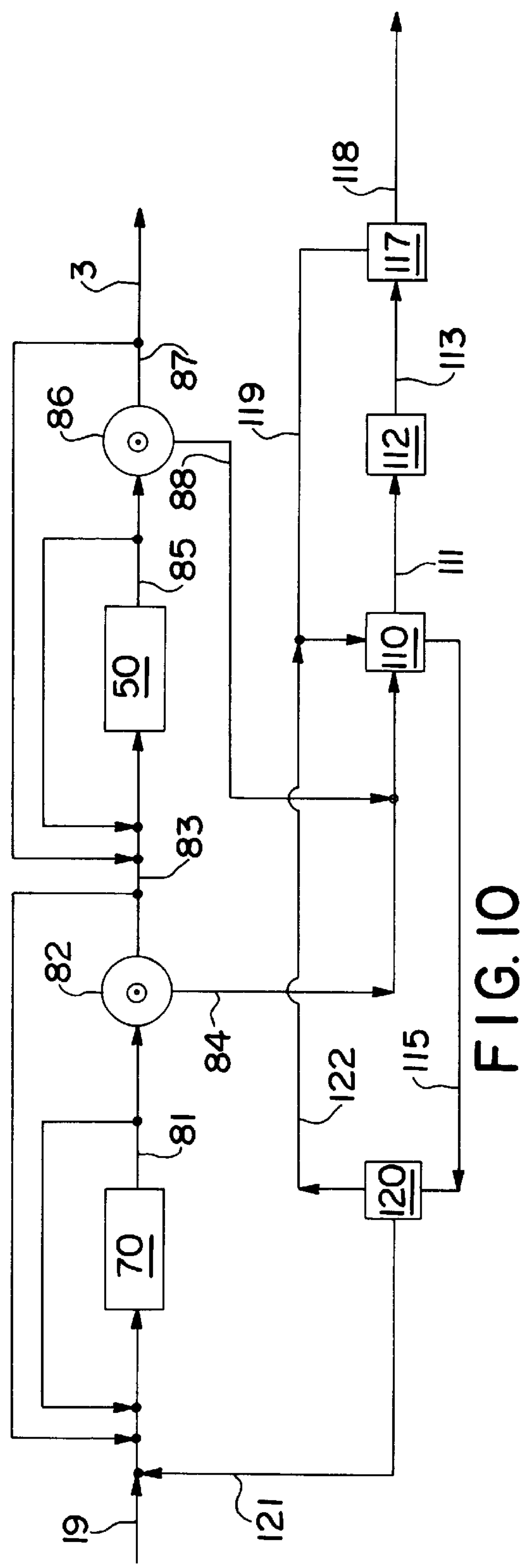

According to FIG. 10, when the washing solvent in the washing column is the desorption solvent (toluene) or another suitable solvent such as pentane, the stream of melted paraxylene containing a minor portion of solvent can be distilled in a distillation unit 117. The paraxylene of very high purity is collected by a line 118 while the light fraction comprising the washing solvent is recycled into the NIRO column. Finally, the washing liquor drawn off by line 15 and containing solvent is distilled in a distillation unit 120, the solvent is recycled at least in part in the column and the washing liquor, freed of the major portion of the solvent, is recycled at least in part to the first crystallization unit by line 121.

The recycling of the mother liquor coming from a crystallization stage A in said stage A or from a stage B in said stage B has been mentioned for a given figure. Of course, these recyclings can apply for all the figures.

Also, it is known that a suspension of crystals coming from a crystallization stage can be recycled to this stage and this recycling can also apply to all the figures (81*a* and 85*a*).

The term of a separation zone has often been used in the description. Of course, it involves at least one centrifuge or at least one rotary filter or at least one column for countercurrent washing by a solvent.

The separation zone where the washing of the crystals is performed can comprise at least one centrifuge or at least one rotary filter. It has been observed, however, that by using, as separation zone where the washing of the crystals is performed, at least one countercurrent washing column, of the NIRO type for example and in particular, with a portion of the very pure melted paraxylene collected, as washing solvent, excellent results were obtained and the cost of the utilities was reduced.

As has been diagrammed in FIG. 1, the mother liquor coming from crystallization unit 5*b* is recycled to adsorption unit 8. In the case of a two-stage or multi-stage crystallization, the mother liquor comes from the coldest crystallization stage after the separation of the paraxylene crystals (line 53, FIG. 5, line 87, FIGS. 7 to 9). The impurities which circulate in the loop of the adsorption, crystallization, isomerization device can be olefinic hydrocarbons, as well as paraffinic and naphthenic hydrocarbons or other oxygenated compounds. They can come in particular, both from the charge to be treated which comes from a catalytic reforming and from the isomerization. These impurities therefore circulate and can be found in all the fractions and particularly in the extract and therefore in the mother liquor resulting from the crystallization step. This mother liquor can be introduced by a line 32 that is connected to line 3 and to line 53 or 87 in at least one clay-treatment reactor 26, advantageously two, placed upstream and connected by a line 27 to adsorption unit 8. Line 1 containing the charge to be treated and line 2 containing the isomerate can be connected to this line 32, the three flows being thus treated in a mixture in a single reactor 26.

According to another variant, charge 1 can have been pretreated in another clay-treatment reactor (not indicated in the figure). It is the same for isomerate 2 which can also have been initially pretreated after having passed into distillation unit 23.

According to a preferred variant, mother liquor 3 can be introduced directly into line 22 leading to distillation unit 23 of the isomerate, before being treated, in mixture with the distilled isomerate, in clay-treatment reactor 26. This variant makes it possible to eliminate approximately all the most volatile compounds, not only from the isomerate but from the mother liquor.

When the distillation unit is adjusted to deliver also, at the bottom, an additional fraction containing most of the heavy compounds (C9+ hydrocarbons, aldehydes, ketones), the clay treatment of the distilled mixture comprising the isomerate and the mother liquor is thereby substantially improved.

A portion of the mother liquor can also be recycled by a line 31 to effluent 27 of reactor 26.

The effluent of the clay-treatment reactor and optionally the crystallization mother liquor 31 that can further contain heavy hydrocarbons, such as hydrocarbons having nine carbon atoms, are introduced by a line 27 into a distilling column 28 which delivers, at the bottom of the column (line 29), the undesirable impurities and, at the top, a distillate corresponding to the purified $C_8$ fraction, that is introduced by line 4 to adsorption unit 8. A portion of the mother liquor can also be introduced into line 4 by a line 30.

These various recyclings can be combined with one another, when it involves, for example, reusing existing pieces of equipment for distillation 23, clay treatment 26 or distillation 28 and when one of these pieces of equipment is already operated at its maximum flow rate or else when it is desired to have the amount of an impurity in the loop lowered without seeking to eliminate it completely. In other words, the mother liquor of the crystallization unit (the coldest stage), conveyed by line 3, can be partially recycled to adsorption unit 8 either directly by means of line 30, or indirectly by means of lines 31, 32 or 33.

So as to keep the amount of constituents with intermediate volatility of the toluene (desorption solvent) at a tolerable level, for example less than 5%, at least one purge of toluene polluted by said constituents is performed by means of a line 35 connected either to line 17, or to line 14 or to line 11 collecting all the solvent recycled to adsorption unit 8.

In addition, it is possible to perform a purge of the mother liquor coming from the crystallization if the amount of constituents with intermediate volatility is too great there. This purge is performed by means of line 34 connected to line 3.

The purge of toluene can be compensated for by an added portion of toluene. Since the greatest sources of $C_8$-aromatic fraction (line 1*a*) come from the catalytic reforming, from dismutation (disproportionation) of the toluene into benzene and xylene and from the toluene—$C_9$-aromatic transalkylation and since the effluents of these units from which they come are in part generally purified in a series of distillation units of which column 28 can be part, it is possible to use, at least in part, as a source of added portion of toluene, either the one produced at the top (line 42) of a distilling column 40 of toluene, before reactor 26 containing the clay, or the one which results from the bypass by a line 1*b* of at least a portion of the charge (line 1) that is mixed with the effluent from the bottom of column 40, or the one which is introduced into the purified charge (line 1) by putting column 40 out of adjustment, which makes it possible to allow the desired proportion of toluene pass into the $C_8$ fraction.

We claim:

1. A process for separating and recovering paraxylene from a charge optionally containing metaxylene, comprising conducting in combination an adsorption operation and a crystallization operation, and subjecting at least a portion of the charge and/or of a mother liquor resulting from said crystallization to a clay treatment operation, whereby at least a portion of olefins in the charge is eliminated.

2. The process according to claim 1, further comprising isomerization delivering an isomerate, and subjecting at least a portion of the isomerate to clay treatment.

3. The process according to claim 2, further comprising subjecting at least a portion of the charge and at least a portion of the isomerate to a clay treatment operation.

4. A process for separating and recovering paraxylene contained in a aromatic hydrocarbon-containing charge, said process, comprising:

(a) contacting a charge containing metaxylene and paraxylene with at least one adsorbent in at least one adsorption zone in the presence of at least one suitable desorption solvent under adsorption conditions such that there is obtained a first fraction containing solvent, metaxylene and optionally ethylbenzene and/or orthoxylene and a second fraction substantially enriched in paraxylene and containing solvent;

(b) distilling the first fraction to recover a mixture of metaxylene and optionally ethylbenzene, and/or orthoxylene;

(c) isomerizing said mixture at least in part under suitable conditions in at least one isomerization zone, recovering an isomerate, and at least partially recycling the isomerate to the adsorption zone;

(d) distilling said second fraction to obtain substantially enriched paraxylene, (e) crystallizing the substantially enriched paraxylene to obtain a mother liquor and paraxylene crystals, and at least partially recycling the mother liquor to the adsorption step, said process further comprising circulating at least one portion of the charge, the isomerate, or the mother liquor, in at least one clay material treatment zone, recovering a first effluent and introducing said first effluent at least in part into the adsorption zone.

5. The process according to claim 4, comprising in (e) crystallizing at +10° to −25° C., to produce paraxylene crystals, and (f) washing said crystals in at least one washing zone with a working solvent.

6. The process according to claim 5, wherein at least a portion of the charge and of the isomerate is circulated in at least one clay treatment zone.

7. The process according to claim 5, wherein at least a portion of the charge, the isomerate and the mother liquor are circulated in one or more clay treatment zones.

8. The process according to claim 5, wherein the adsorption zone is a simulated moving bed.

9. The process according to claim 5, further comprising introducing at least a portion of the mother liquor into a distilling column downstream from the isomerization zone, distilling the isomerate and the mother liquor to obtain a top fraction containing light compounds and an additional fraction containing a mixture of said distilled mother liquor and a distilled isomerate, introducing said additional fraction into the clay treatment zone, and recovering a second effluent.

10. The process according to claim 9, further comprising drawing off a bottom fraction containing heavy compounds from the distilling column.

11. The process according to claim 5, further comprising mixing a portion of the mother liquor with the first effluent of the clay treatment zone and a subsequent effluent.

12. The process according to claim 5, further comprising distilling the first effluent from the clay treatment zone in at least one distilling column which delivers a bottom fraction containing heavy compounds and a top fraction, and introducing said top fraction into the adsorption zone.

13. The process according to claim 5, wherein the clay is an activated natural aluminosilicate, the temperature is from 100 to 300° C., the pressure is from 3 to 100 bar, and the hourly space velocity is 1 to 8.

14. The process according to claim 5, further comprising purging at least a portion of the mother liquor before introduction into the clay treatment zone.

15. The process according to claim 5, further comprising purging the desorption solvent resulting from (b) and (d) at least in part, before recycling, and compensating for the purge of the solvent by an addition of fresh solvent, either into the charge or upstream from the adsorption zone.

16. The process according to claim 5, further comprising crystallizing the paraxylene of (d) in a single stage, recovering a suspension of crystals in mother liquor, separating the crystals from the mother liquor in a separation zone, washing the crystals obtained with washing solvent, recovering a washing liquor, recycling at least a portion of the washing liquor and completely melting the paraxylene crystals so as to obtain a liquid stream of melted paraxylene.

17. The process according to claim 16, wherein separating and washing is conducted in at least one countercurrent washing column into which at least a portion of the liquid stream of melted paraxylene is introduced as washing solvent and in which the mother liquor and the washing liquor are the same liquor and are recycled at least in part to the adsorption zone and optionally in part to the crystallization zone.

18. The process according to claim 16, wherein separating and washing is conducted in at least one centrifuge or at least one rotary filter, said process further comprising introducing at least a portion of the melted paraxylene as washing solvent and recycling the mother liquor and the washing liquor to the adsorption zone and optionally in part to the crystallization zone.

19. The process according to claim 16, wherein the washing solvent is the desorption solvent, said process further comprising distilling a liquid stream of paraxylene recovering, in a top fraction, washing solvent, recycling said solvent at least in part to the washing zone of the crystals, and recovering, in a bottom fraction, liquid paraxylene, either (i) distilling the mother liquor comprising washing solvent and recycling to the adsorption zone and optionally in part to the crystallization zone, when the washing zone is a countercurrent washing column, or (ii) recycling the mother liquor to the adsorption zone and optionally in part to the crystallization zone and the washing liquor into a distillation zone according to (b) when the washing zone is a centrifuge or a rotary filter.

20. The process according to claim 16, wherein the washing solvent is a solvent other than the liquid stream of melted paraxylene and desorption solvent, comprising distilling the liquid stream of melted paraxylene so as to recover, at the top, washing solvent and recycling said solvent at least in part to the washing zone of the crystals, and recovering at the bottom, liquid paraxylene of very high purity and either (i) distilling and recycling the mother liquor comprising the washing liquor to the adsorption zone and optionally in part to the crystallization zone, and recycling the solvent to the washing zone, when the washing zone is a countercurrent washing zone, or (ii) recycling the mother liquor to the adsorption zone and optionally in part to the crystallization zone, distilling and recycling the washing liquor to the adsorption zone and optionally in part to the crystallization zone, and recycling the solvent to the washing zone, when the washing zone is a centrifuge or a rotary filter.

21. The process according to claim 5, comprising performing a first crystallization or the paraxylene of (d) in a first crystallization zone at a temperature T1, recovering a suspension of first paraxylene crystals in a first mother liquor, separating the first crystals from the first mother liquor in a first separation zone, recycling at least a portion of the first mother liquor to the adsorption zone, completely melting the separated first crystals and crystallizing in a second crystallization zone at a temperature T2 that is higher than T1, recovering a suspension of second paraxylene crystals in a second mother liquor, separating the second crystals from the second mother liquor in a second separation zone, washing the second crystals with a washing solvent in the second separation zone, recovering a washing liquor, recycling the second mother liquor, at least in part, and at least a portion of the washing liquor to the first crystallization zone and optionally in part to the second crystallization zone, and completely melting the second paraxylene crystals so as to obtain a liquid stream of melted paraxylene.

22. The process according to claim 21, wherein the washing solvent is a portion of the liquid stream of melted paraxylene and the washing liquor and the second mother liquor are one and the same liquor that is recycled to the first crystallization zone and optionally in part to the second crystallization zone.

23. The process according to claim 21, wherein the washing solvent is the desorption solvent, said process further comprising distilling the stream of melted paraxylene so as to recover, in a top fraction, washing solvent, recycling said solvent at least in part to the second separation zone, and recovering, in a bottom fraction, liquid paraxylene of very high purity, and either (i) distilling the second mother liquor containing the washing liquor before recycling when the second separation zone is a countercurrent washing column, or (ii) distilling the washing liquor before recycling to the first crystallization unit and/or to the second crystallization unit when the second separation zone is a centrifuge or a rotary filter.

24. The process according to claim 21, wherein the washing solvent is a solvent other than the stream of melted paraxylene and the desorption solvent, said process further comprising distilling the stream of melted paraxylene coming from the suspension of second crystals, recovering washing solvent in a top fraction, recycling said solvent at least in part to the second separation zone and recovering liquid paraxylene of very high purity in a bottom fraction, and either (i) distilling the mother liquor comprising the washing liquor and recycling it to the first crystallization zone and optionally in part to the second crystallization zone when the second separation zone is a countercurrent column, or (ii) recycling the mother liquor to the first crystallization zone and optionally in part to the second crystallization zone, and distilling the washing liquor and recycling it to the first crystallization zone and optionally in part to the second crystallization zone, when the second separation zone is a centrifuge or a rotary filter.

25. The process according to claim 5, wherein (e) comprises performing a first crystallization of the paraxylene of (d) in a first crystallization zone at a temperature T1, recovering a suspension of first paraxylene crystals in a first mother liquor, separating the first crystals from the first mother liquor in a first separation zone, optionally washing the first crystals with the washing solvent in the first separation zone, crystallizing at least a portion of the first mother liquor in a second crystallization zone at a temperature T2 that is lower than temperature T1, recovering a suspension of second paraxylene crystals in a second mother liquor, separating the second crystals from the second mother liquor in a second separation zone, washing the second crystals with the washing solvent in the second separation zone, recovering a second mother liquor and recycling said mother liquor at least in part to the adsorption zone, mixing the first and second paraxylene crystals, completely melting said crystals and recovering a stream of melted paraxylene.

26. The process according to claim 25, further comprising drawing off at least a portion of the stream of melted paraxylene and using said portion as washing solvent in the first separation zone and in the second separation zone.

27. The process according to claim 25, wherein the washing solvent is the desorption solvent, said process further comprising distilling the stream of melted paraxylene, recycling at least in part, a top fraction containing washing solvent to the first and second separation zones, and recovering a bottom fraction containing liquid paraxylene of very high purity.

28. The process according to claim 5, where (e) comprising performing a first crystallization of the paraxylene of (d) and of optionally melted recycled crystals coming from a second crystallization in a first crystallization zone at a temperature T1, recovering a suspension of paraxylene crystals in a first mother liquor, separating the crystals from the first mother liquor in a first separation zone, washing said crystals, recovering a stream of melted paraxylene, crystallizing at least a portion of the first mother liquor in a second crystallization zone at a temperature T2 that is lower than temperature T1, recovering a suspension of second paraxylene crystals in a second mother liquor, separating the second crystals from the second mother liquor in a second separation zone, recovering a second mother liquor (87) and recycling said second mother liquor at least in part to the adsorption zone, optionally melting the second crystals and recycling the optionally melted crystals to the first crystallization zone and recrystallizing said melted crystals with the paraxylene of (d) at temperature T1.

29. The process according to claim 5, wherein (e) comprises performing a first crystallization of the paraxylene of (d) and of optionally melted recycled crystals coming from a second crystallization in a first crystallization zone at a temperature T1, recovering a suspension of paraxylene crystals in a first mother liquor, separating the crystals from the first mother liquor in a first separation zone, washing said crystals, melting said crystals and recovering a stream of melted paraxylene, crystallizing at least a portion of the first mother liquor in a second crystallization zone at a temperature T2 that is lower than temperature T1, recovering a suspension of second paraxylene crystals in a second mother liquor, separating the second crystals from the second mother liquor in a second separation zone, recovering a second mother liquor, recycling said second mother liquor at least in part to the adsorption zone, partially melting the second crystals, recycling a slurry of partially melted crystals to the first crystallization zone, and recrystallizing said slurry with the paraxylene of (d) at temperature T1.

30. The process according to claim 28, wherein at least a portion of the stream of melted paraxylene coming from the first separation zone is used as washing solvent.

31. The process according to claim 28, wherein the washing solvent is the desorption solvent and wherein the stream of melted paraxylene coming from the first crystallization zone is distilled, said process further comprising recovering washing solvent in a top fraction recycling said solvent at least in part to the first separation zone, and recovering liquid paraxylene in a bottom fraction.

32. The process according to claim 5, wherein (e) comprises performing a first crystallization of the paraxylene of (d) in a first crystallization zone at a temperature T1, recovering a suspension of first paraxylene crystals in a first mother liquor, separating the first crystals from the first mother liquor in a first separation zone, crystallizing at least a portion of the first mother liquor in a second crystallization zone at a temperature T2 that is lower than T1, separating second crystals from a second mother liquor in a second separation zone, recovering the second mother liquor, recycling said second mother liquor at least in part to the adsorption zone, recovering the first crystals and the second crystals, and washing in at least one separation and countercurrent washing zone with washing solvent, recycling a recovered a washing liquor at least in part to the first crystallization zone, recovering paraxylene crystals, melting said crystals completely in a melting zone and collecting a stream of melted paraxylene.

33. The process according to claim 32, wherein a portion of the stream of melted paraxylene is drawn off and used as washing solvent.

34. The process according to claim 32, wherein the washing solvent is the desorption solvent, said process further comprising distilling the stream of melted paraxylene, recycling collected washing solvent at least in part in the washing zone, distilling the washing liquor and recycling it to the first crystallization zone and recycling, at least in part, the washing solvent in the washing zone.

35. The process according to claim 21, further comprising recycling a portion of the first mother liquor to the first crystallization zone and a portion of the second mother liquor to the second crystallization zone.

36. The process according to claim 5, wherein the separation zone where the washing of the crystals is performed comprises at least one counter current washing column.

37. The process according to claim 5, wherein the separation zone where the washing of the crystals is performed comprises at least one centrifuge or at least one rotary filter.

38. The process according to claim 5, wherein said desorption solvent is toluene, said process further comprising circulating a portion of the charge in a distillation column to draw off toluene at least in part, and introducing said toluene as an added portion of desorption solvent.

39. A process for separating and recovering paraxylene from a charge containing paraxylene and optionally metaxylene, said process comprising, in combination, an adsorption operation and a crystallization operation, wherein at least a portion of the mother liquor coming from the crystallization operation is purified by distillation before being recycled to the adsorption operation.

40. The process according to claim 39, comprising in combination, in addition to the adsorption and crystallization operations, an isomerization operation, wherein at least a portion of isomerate and at least a portion of said mother liquor simultaneously undergo a purification operation by distillation.

41. A process for separating and recovering paraxylene contained in a charge of hydrocarbons comprising $C_8$-aromatic hydrocarbons, the process comprising:

a) contacting said charge containing metaxylene, paraxylene and optionally ethylbenzene and/or orthoxylene with an adsorbent in the presence of a desorption solvent in at least one adsorption zone under adsorption conditions such that there is obtained a first fraction containing solvent, metaxylene and optionally ethylbenzene and/or orthoxylene and a second fraction containing solvent and essentially substantially enriched paraxylene;

b) distilling the first fraction to separate the solvent and the mixture of metaxylene and optionally ethylbenzene, and/or orthoxylene;

c) isomerizing said mixture of metaxylene and optionally ethylbenzene under suitable conditions in an isomerization zone, recovering an isomerate and recycling said isomerizate at least in part to a);

d) distilling the second fraction and recovering the solvent and substantially enriched paraxylene;

e) crystallizing the paraxylene of d) in at least one crystallization zone at high temperature, separating a mother liquor and paraxylene crystals saturated with mother liquor, and recycling said mother liquor at least in part to a); and f) washing the paraxylene crystals with a washing solvent in at least one washing zone and recovering paraxylene crystals;

wherein at least a portion of the mother liquor is introduced into a distillation column, a fraction containing purified mother liquor reduced in solvent is obtained, and recycled into the adsorption zone.

42. The process according to claim 41, further comprising introducing at least a portion of the mother liquor into the distillation column downstream from the isomerization zone, distilling the isomerate and the mother liquor, obtaining a top fraction containing light compounds and a fraction containing a mixture of said distilled mother liquor and a distilled isomerate, and recycling said fraction into the adsorption zone.

43. The process according to claim 5, wherein the desorption solvent is either toluene or paradiethylbenzene.

44. The process according to claim 9, further comprising mixing a portion of the mother liquor with the first or second effluent of the clay treatment zone and a third effluent.

45. The process according to claim 11, further comprising distilling the first, second or third effluent from the clay treatment zone in at least one distilling column which delivers a bottom fraction containing heavy compounds and a top fraction, and introducing said top fraction into the adsorption zone.

46. The process according to claim 42, wherein the desorption solvent is either toluene or paradiethylbenzene.

* * * * *